(12) United States Patent
Chemburkar et al.

(10) Patent No.: US 6,372,905 B1
(45) Date of Patent: Apr. 16, 2002

(54) PROCESSES AND INTERMEDIATES FOR PREPARING RETROVIRAL PROTEASE INHIBITORS

(75) Inventors: Sanjay R. Chemburkar, Gurnee; Ketan M. Patel, Wheeling, both of IL (US); Harry O. Spiwek, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/942,344

(22) Filed: Aug. 29, 2001

Related U.S. Application Data

(60) Provisional application No. 60/229,212, filed on Aug. 31, 2000.

(51) Int. Cl.$^7$ ............................................. C07D 239/36
(52) U.S. Cl. ...................................................... 544/316
(58) Field of Search .......................................... 544/316

(56) References Cited

U.S. PATENT DOCUMENTS 5,914,332 A    6/1999   Sham et al. ................. 514/274

Primary Examiner—John M. Ford
(74) Attorney, Agent, or Firm—Steven R. Crowley

(57) ABSTRACT

The instant invention provides processes and intermediates employed in the synthesis of ((2S,3S,5S)-2-(2,6-dimethylphenoxyacetyl)-amino-3-hydroxy-5-(2S-(1-tetrahydropyrimid-2-onyl)-3-methyl-butanoyl)amino-1,6-diphenylhexane and analogs thereof.

13 Claims, No Drawings

PROCESSES AND INTERMEDIATES FOR PREPARING RETROVIRAL PROTEASE INHIBITORS

This application claims the benefit of U.S. Provisional Application for Patent No. 60/229,212, filed Aug. 31, 2000.

TECHNICAL FIELD

The present invention relates to processes and intermediates employed in the synthesis of HIV protease inhibitors.

BACKGROUND OF THE INVENTION

Compounds that are inhibitors of human immunodeficiency virus (HIV) protease are useful for inhibiting HIV protease in vitro and in vivo and are useful for inhibiting an HIV infection. Examples of HIV protease inhibitors include the compound of formula I:

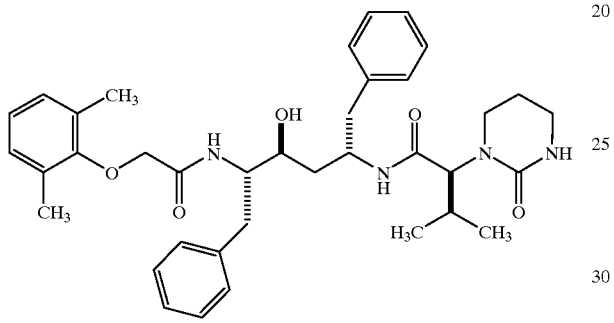

which is also known as ((2S,3S,5S)-2-(2,6-dimethylphenoxyacetyl)-amino-3-hydroxy-5-(2S-(1-tetrahydropyrimid-2-onyl)-3-methylbutanoyl)amino-1,6-diphenylhexane or lopinavir. Processes for preparing compounds of formula I and analogs thereof are provided in U.S. Pat. No. 5,914,332, issued Jun. 22, 1999, which is herein incorporated by reference.

An intermediate which is useful for preparing the compounds of formula I and analogs thereof is a compound of formula II:

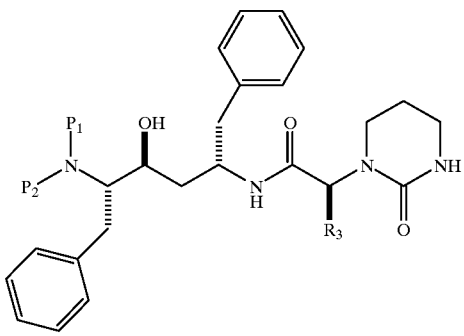

wherein $R_3$ is loweralkyl, hydroxyalkyl or cycloalkylalkyl and $P_1$ and $P_2$ are independently selected from hydrogen and an N-protecting group. Preferred compounds of formula II are those wherein $R_3$ is loweralkyl, $P_1$ and $P_2$ are hydrogen or $P_1$ and $P_2$ are benzyl. More preferred compounds of formula II are those wherein $R_3$ is isopropyl and $P_1$ and $P_2$ are hydrogen or wherein $R_3$ is is isopropyl and $P_1$ and $P_2$ are benzyl.

Methods for the preparation of a compound of formula II are disclosed in U.S. Pat. No. 5,914,332. These methods involve the reaction of a compound of the formula III:

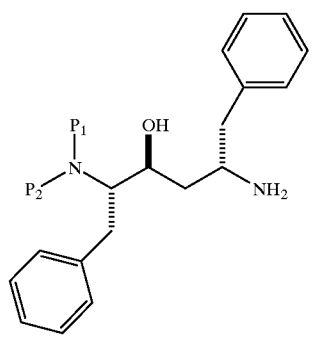

wherein $P_1$ is hydrogen or an N-protecting group and $P_2$ is an N-protecting group With a compound of the formula IV:

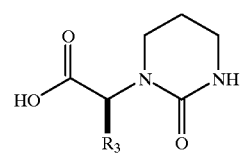

wherein $R_3$ is loweralkyl, hydroxyalkyl or cycloalkylalkyl; or a salt or an activated ester thereof.

Preferred compounds of the formula III are those wherein $P_1$ and $P_2$ are N-protecting groups. Most preferred compounds of the formula III are those wherein $P_1$ and $P_2$ are both benzyl. Most highly preferred is the compound of formula III that is (2S,3S,5S)-2-N,N-dibenzylamino-3-hydroxy-5-amino-1,6-diphenylhexane.

Preferred compounds of the formula IV are those wherein $R_3$ is loweralkyl. Most preferred compounds of the formula IV are those wherein $R_3$ is isopropyl. Also preferred are the acid chloride derivatives of the compounds of formula IV. Most highly preferred is the compound of formula IV that is 2S-(1-tetrahydro-pyrimid-2-only)-3-methyl butanoic acid and the compound of formula IV that is 2S-(1-tetrahydro-pyrimid-2-only)-3-methyl butanoyl chloride.

In the disclosed process, (2S,3S,5S)-2-N,N-dibenzylamino-3-hydroxy-5-amino-1,6-diphenylhexane is reacted with 2S-(1-tetrahydro-pyrimid-2-only)-3-methyl butanoyl chloride in a suitable solvent (ethyl acetate or ethyl acetate/DMF) with imidazole as a base. However, this process is not suited for large-scale production for many reasons, including unstable intermediates, low yields, and catalyst poisoning. In particular, the acid chloride is relatively unstable and the use of thionyl chloride to prepare the acid chloride leads to impurities that poison the catalyst used in a later reaction. In addition, some racemization of the amino acid side chain occurs under the reaction conditions used.

Thus, there is a continuing need for improved processes for preparing intermediates employed in the synthesis of HIV protease inhibitors, including compounds of formula I as defined hereinabove.

DISCLOSURE OF THE INVENTION

The present invention relates to processes and intermediates for preparing a compound of formula II:

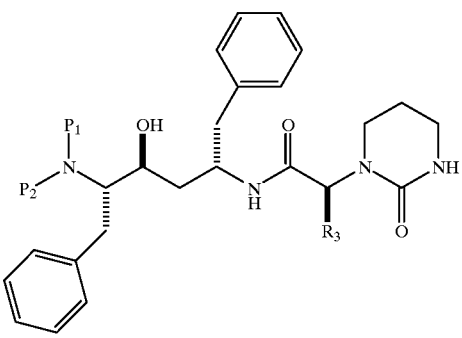

wherein $R_3$ is loweralkyl, hydroxyalkyl or cycloalkylalkyl and $P_1$ and $P_2$ are independently selected from hydrogen and an N-protecting group comprising reacting a compound of the formula III:

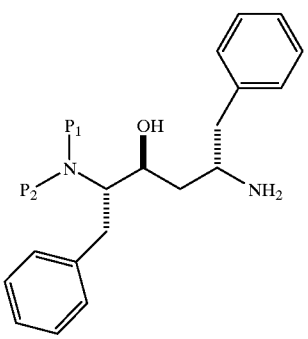

wherein $P_1$ is hydrogen or an N-protecting group and $P_2$ is an N-protecting group with a compound of the formula V:

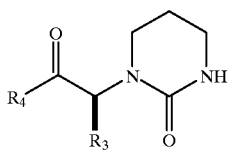

wherein $R_3$ is loweralkyl, hydroxyalkyl or cycloalkylalkyl and $R_4$ is a nitrogen-containing heterocycle, bonded through a ring nitrogen atom to the carbonyl group, selected from the group consisting of imidazolyl, pyrrolyl, pyrazolyl, 1,2,3-triazolyl, 1,2,4-triazolyl, tetrazolyl, indolyl, benzimidazolyl and benzotriazolyl.

In a preferred process of the invention, $P_1$ and $P_2$ are N-protecting groups, $R_3$ is loweralkyl and $R_4$ is imidazolyl. In a most preferred process of the invention, $P_1$ and $P_2$ are both benzyl, $R_3$ is isopropyl and $R_4$ is imidazolyl.

In the process of the invention, the compound of formula III is reacted with the compound of formula V in a molar ratio of from about 1.0 moles of the compound of formula III to about 1.3 moles of the compound of formula V. A preferred ratio is from about 1.0 to about 1.2. A most preferred ratio is from about 1.0 to about 1.15.

Suitable solvents for the process of the invention are inert solvents, such as isopropyl acetate, ethyl acetate, tetrahydrofuran (THF), methyl t-butyl ether and the like. A preferred solvent for the process of the invention is ethyl acetate.

The process of the invention can be carried out at a temperature of from about 15° C. to about 100° C. The preferred temperature for the process of the invention is about the reflux temperature of the solvent. The most preferred temperature for the process of the invention is from about 75° C. to about 80° C.

The process of the invention is accelerated by the presence of water. The preferred amount of water present in the reaction mixture is from about 1% to about 3% (weight/volume), based on the ratio of the amount of water (in grams) to the total volume (in mL) of the reaction mixture.

The compound of formula V is prepared by reaction of carboxylic acid IV (about 1.00 moles) with carbonyldiimidazole (about 1.05 moles) in an inert, aprotic solvent such as isopropyl acetate, ethyl acetate, tetrahydrofuran (THF), methyl t-butyl ether and the like at a temperature of from about 15° C. to about 50° C. Preferably, carboxylic acid IV is reacted with $R_4$—C(O)—$R_4$, $R_4$—C(S)—$R_4$ or $R_4$—S(O)—$R_4$ wherein $R_4$ is defined as above (preferably, carbonyldiimidazole) in ethyl acetate at about 15° C.

While the compound of formula V can be isolated, preferably it is prepared and then reacted (without isolation and purification) with the compound of formula III in a one-pot process.

The compound of formula II wherein $P_1$ and $P_2$ are each benzyl can then be debenzylated and the resulting compound of formula II wherein $P_1$ and $P_2$ are each hydrogen (as the (S)-pyroglutamic acid salt) can be reacted with 2,6-dimethylphenoxyacetyl chloride (as disclosed in U.S. Pat. No. 5,914,332) to provide lopinavir.

The term "loweralkyl" as used herein refers to straight or branched chain hydrocarbon radicals containing from 1 to 6 carbon atoms. Representative examples of loweralkyl groups include groups such as, for example, methyl, ethyl, n-propyl, iso-propyl, n-butyl, iso-butyl, sec-butyl, t-butyl n-pentyl, 1-methylbutyl, 2,2-dimethylbutyl, 2-methylpentyl, 2,2-dimethylpropyl, n-hexyl, and the like.

The term "cycloalkyl" as used herein refers to an aliphatic ring system having 3 to 10 carbon atoms and 1 or 2 rings. Representative cylcoalkyl groups include, for example, cyclopropyl, cyclobutyl, cyclopentyl, cyclohexyl, cycloheptyl, norbornane, bicyclo[2.2.2]octane and the like.

The term "(cycloalkyl)alkyl" as used herein refers to a cycloalkyl group appended to a loweralkyl radical. Representative examples of (cycloalkyl)alkyl groups include groups such as, for example, cyclohexylmethyl, cyclopentylmethyl, cyclohexylethyl, cyclopentylethyl, and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis*, 2nd edition, John Wiley & Sons, New York (1991). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfenyl (phenyl-S—), triphenylmethylsulfenyl (trityl-S—) and the like; sulfinyl groups such as p-methylphenylsulfinyl (p-methylphenyl-S(O)—), t-butylsulfinyl (t-Bu-S(O)—) and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include benzyl and the like.

The following Examples are provided to further illustrate the present invention.

EXAMPLE 1

(2S,3S,5S)-2-N,N-dibenzylamino-3-hydroxy-5-(2S-(1-tetrahydropyrimid-2-onyl)-3-methylbutanoyl) amino-1,6-diphenylhexane A. (2S,3S,5S)-2-N,N-dibenzylamino-3-hydroxy-5-amino-1,6-diphenylhexane 11.5 grams of sodium borohydride was suspended in 292 grams of ethylene glycol dimethyl ether (DME) and cooled to not less than −5° C. In a second flask, 70.4 grams of methane sulfonic acid (MSA) was slowly added to 28.0 grams ethylene glycol dimethyl ether maintaining the temperature at not more than 35° C. The MSA solution was cooled to not more than 25° C. and transferred to the sodium borohydride suspension maintaining the temperature at not more than 5° C. In a separate flask, 50 gm of 2-amino-5S-dibenzylamino-4-oxo-1,6-diphenylhexane (U.S. Pat. No. 5,491,253) was dissolved in a mixture of 91.7 grams of ethylene glycol dimethyl ether and 50.0 grams of isopropyl alcohol. This solution was transferred to the sodium borohydride/MSA solution maintaining the temperature at not more than 25° C. The contents of the flask was stirred for not less than 1 hour at 15 to 25° C. Then the contents were cooled to not more than −3° C. and 53.0 grams of triethanolamine was added maintaining the temperature at not more than 5° C. The mixture was stirred for not less than 15 minutes and a solution of 7.1 grams of sodium borohydride in 79.4 grams of dimethylacetamide was added maintaining the temperature at not more than 10° C. Then 240.2 grams of distilled water was added and the contents mixed at 10 to 30° C. for not less than 30 minutes. 121.2 grams of methyl t-butyl ether were added and the mixture stirred for not less than 30 minutes. The layers were allowed to separate and the aqueous layer was discarded. The organic layer was washed with sodium hydroxide solution prepared from 16.5 grams of sodium hydroxide and 150.2 grams of distilled water. The layers were allowed to separate and the aqueous layer was discarded. The organic layer was washed with sodium chloride solution prepared from 16.5 grams of sodium chloride and 109.7 grams of distilled water. The layers were allowed to separate and the aqueous layer discarded. The organic layer was distilled under vacuum (50–100 mm Hg) at not more than 75° C. The residue was dissolved in 196.5 grams of ethyl acetate. 5.0 grams of distilled water was added.

B. N-(2S-(1-tetrahydro-pyrimid-2-onyl)-3-methyl butanoyl)imidazole

A mixture containing 24.8 grams 2S-(1-tetrahydro-pyrimid-2-only)-3-methyl butanoic acid (U.S. Pat. No. 5,914,332) and 21.0 grams of carbonyl diimidazole in 147.5 grams of ethyl acetate was stirred at 15 to 25° C. for not less than 1 hour.

C. (2S,3S,5S)-2-N,N-dibenzylamino-3-hydroxy-5-(2S-(1-tetrahydro-pyrimid-2-onyl)-3-methylbutanoyl)amino-1,6-diphenylhexane 0.6 grams of distilled water was added to the solution resulting from Example 1, step B and the contents stirred for not less than 15 minutes. The solution resulting from Example 1, step A was heated to reflux. The solution resulting from Example 1, step B was transferred to the flask containing the refluxing solution resulting from Example 1, step A and stirred at reflux for not less than 1 hour. The reaction was cooled to room temperature and 246.2 grams of distilled water was added. The solution was stirred for not less than 15 minutes and the aqueous layer was separated and discarded. The organic layer was washed 3 additional times using 246.2 grams of distilled water each wash. The organic layer was then distilled under vacuum (50–100 mm Hg) at not more than 75° C. to give the desired product.

EXAMPLE 2

((2S,3S,5S)-2-(2,6-dimethylphenoxyacetyl)-amino-3-hydroxy-5-(2S-(1-tetrahydropyrimid-2-onyl)-3-methyl-butanoyl)amino-1,6-diphenylhexane A. (2S,3S,5S)-2-amino-3-hydroxy-5-(2S-(1-tetrahydro-pyrimid-2-onyl)-3-methylbutanoyl) amino-1,6-diphenylhexane The product of Example 1, step C was dissolved in 307.5 grams of methanol with heating to 55° C., if necessary. After adding 21.8 grams of ammonium formate and 6.9 grams of palladium on carbon to the solution, the reaction was stirred at 50 to 60° C. for not less than 2 hours. The contents were filtered through a pad of filter aid. The flask and filter were rinsed with 85.6 grams of methanol. The combined filtrates were distilled under vacuum (50–100 mm Hg) at not more than 75° C. The residue was dissolved in 171.3 grams of ethyl acetate, with heating to 50° C., if necessary, and concentrated under vacuum (50–100 mm Hg) at not more than 75° C. The residue was dissolved in 262.1 grams of ethyl acetate, with heating to 50° C., if necessary. A sample was analyzed for moisture to meet limit of 0.2%, repeating distillation and ethyl acetate addition if the limit was not met. Distillation of the solvent provided the desired compound.

B. (2S,3S,5S)-2-amino-3-hydroxy-5-(2S-(1-tetrahydro-pyrimid-2-onyl)-3-methylbutanoyl) amino-1,6-diphenylhexane (S-pyroglutamic acid salt)

The product of Example 2, step A was dissolved in 262.1 grams of ethyl acetate, with heating to 50° C., if necessary. 79.6 grams of dimethylformamide was added and the solution was heated to 52° C. A solution of 14.6 grams of S-pyroglutamic acid in 30.0 grams of dimethylformamide was added, maintaining the temperature at 52° C. The mixture was stirred at 52° C. until the pyroglutamate salt precipitated. If precipitation did not start, the batch could be seeded using 0.05 grams of (2S,3S,5S)-2-amino-3-hydroxy-5-(2S-(1-tetrahydro-pyrimid-2-onyl)-3-methylbutanoyl) amino-1,6-diphenylhexane (S-pyroglutamic acid salt) seed crystals (U.S. Pat. No. 5,914,332). Once precipitation started, the batch was stirred at 52° C. for not less than 1 hour, then cooled to 20° C. and stirred for not less than 5 hours. The precipitate was collected by filtration and washed with 128.5 grams of ethyl acetate. The solid was dried in a vacuum oven under vacuum (50–100 mm Hg) at not more than 65° C. to give 55.6 grams of the desired compound.

C. ((2S,3S,5S)-2-(2,6-dimethylphenoxyacetyl)-amino-3-hydroxy-5-(2S-(1-tetrahydropyrimid-2-onyl)-3-methyl-butanoyl)amino-1,6-diphenylhexane The product of Example 2, step B is reacted with 2,6-dimethylphenoxy-acetyl chloride according to the method described in U.S. Pat. No. 5,914,332 to provide the desired product.

EXAMPLE 3

(2S,3S,5S)-2-amino-3-hydroxy-5-(2S-(1-tetrahydro-pyrimid-2-onyl)-3-methylbutanoyl)amino-1,6-diphenylhexane

A. (2S,3S,5S)-2-N,N-dibenzylamino-3-hydroxy-5-amino-1,6-diphenylhexane

Charged 560 L of ethylene glycol dimethyl ether into reactor A (1,000 L, glass lined). While stirring, cooled the contents of the reactor to not more than 5° C. Charged 104 kg of sodium borohydride into reactor B (10,000 L, stainless steel). Chunks of sodium borohydride were broken up before charging to the reactor. Charged 2400 L of ethylene glycol dimethyl ether to the reactor B containing the sodium borohydride. While stirring, cooled the contents of reactor B to not more than −10° C. Charged 624 kg of methane-sulfonic acid to reactor A, while maintaining an internal temperature of not more than 30° C. during the addition.

Under a nitrogen atmosphere, charged 400 kg of 2-amino-5-S-dibenzylamino-4-oxo-1,6-diphenylhex-2-ene into reactor C (3,500 L, stainless steel). Charged 850 L of ethylene glycol dimethyl ether into reactor C. Charge 510 L of isopropyl alcohol into reactor C. Mixed the contents of reactor C until the solids were in solution.

Transferred the contents of reactor A into reactor B while maintaining a temperature of not more than 5° C. in reactor B. Transferred the contents of reactor C into reactor B while maintaining a temperature of not more than 25° C. in reactor B. After the addition was complete, the temperature of the contents of reactor B was adjusted to 20° C.±5° C.

Charged 250 L of ethylene glycol dimethyl ether into reactor C and then transferred the contents of reactor C into reactor B. The contents of reactor B were stirred for not less than 6 hours at 20° C.±5° C. The contents of reactor B were then cooled to not more than −3° C.

Under a nitrogen atmosphere, charged reactor C with 57 kg of sodium borohydride. Chunks of sodium borohydride were broken up before charging to the reactor. Using a pump, charged 635 kg of dimethylacetamide into reactor C with stirring. Using a pump, charged 424 kg of triethanolamine into reactor B while maintaining the temperature of the contents of reactor B at not more than 5° C. After the addition was complete, the contents of reactor B were cooled to not more than −3° C.

The contents of reactor C were transferred to reactor B while maintaining the temperature of the contents of reactor B at not more than 10° C. After the addition was complete, the temperature of the contents of reactor B was adjusted to 15° C.±5° C. and stirred for not less than 1 hour at 15° C.±5° C.

Under a nitrogen atmosphere, charged reactor D (12,000 L, stainless steel) with 1920 L of water and cooled the reactor jacket to 5° C.±5° C. While stirring the contents of reactor D, transferred the contents of reactor B to reactor D while maintaining the temperature of the contents of reactor D at not more than 30° C. Charged 100 L of ethylene glycol dimethyl ether to reactor B, then transferred the contents of reactor B to reactor D.

Stirred the contents of reactor D at 20° C.±5° C. for not less than 30 minutes. Then discontinued stirring and allowed the contents of reactor D to settle for not less than 1 hour. Separated the lower layer in reactor D into reactor E (1,000 L, stainless steel). Charged 1310 L of methyl tert-butyl ether into reactor E and stirred the contents of reactor E at 20° C.±5° C. for not less than 15 minutes. After stirring, the contents of reactor E were allowed to settle for not less than 1 hour. The lower layer in reactor E was separated and removed.

The contents of reactor E were transferred into reactor D. The contents of reactor D were stirred for not less than 15 minutes. After stirring was complete, the contents of reactor D were allowed to settle for not less than 15 minutes. The lower layer in reactor D was separated and removed.

Charged 1200 L of water into reactor E. Charged 132 kg of sodium hydroxide pellets into reactor E. The contents of reactor E were stirred until all of the solids were dissolved.

The contents of reactor E were then transferred to reactor D and the contents of reactor D Were stirred for not less than 15 minutes. Then the contents of reactor D were allowed to settle for not less than 15 minutes. The lower aqueous layer in reactor D was separated and removed.

Charged 880 L of water to reactor E. Charged 132 kg of sodium chloride to reactor E, followed by stirring until all of the solids were dissolved. Then the contents of reactor E were transferred to reactor D. The contents of reactor D were stirred for not less than 15 minutes and then allowed to settle for not less than 30 minutes. The lower layer in reactor D was separated and removed.

The contents of reactor D were distilled under vacuum (50–100 mm Hg) at a maximum jacket temperature of 75° C. until no more distillate came off. Charged 1740 L of ethyl acetate into reactor D and stirred at not more than 50° C. until all solids were dissolved. When all solids were dissolved, the contents of reactor D were cooled to 20° C.±5° C.

B. N-(2S-(1-tetrahydro-pyrimid-2-onyl)-3-methyl butanoyl)imidazole

Under a nitrogen atmosphere, charged reactor G (6,000 L, glass lined) with 199 kg of N-(2S-(1-tetrahydro-pyrimid-2-onyl)-3-methyl butanoic acid (U.S. Pat. No. 5,914,332). Charged 175 kg of carbonyl diimidazole into reactor G. Charged 1320 L of ethyl acetate into reactor G and stirred contents of reactor G for not less than 1 hour at 20° C.±5° C.

C. (2S,3S,5S)-2-amino-3-hydroxy-5-(2S-(1-tetrahydro-pyrimid-2-onyl)-3-methylbutanoyl)amino-1,6-diphenylhexane Charged 30 kg of water into reactor D and stirred the contents of reactor D for not less than 10 minutes. Then adjusted the temperature of reactor D to reflux (approximately 75–77° C.). After the contents of reactor D reached reflux, charged 4.6 kg of water to reactor G and stirred contents of reactor G for not less than 15 minutes. Then transferred contents of reactor G to reactor D. Charged 430 L of ethyl acetate to reactor G and then transferred the contents of reactor G to reactor D. Then the temperature of reactor D was readjusted to reflux the contents. The contents of reactor D were stirred at reflux for not less than 1 hour.

Charged 1970 L of water into reactor D. Waited for the contents of reactor D to cool to within the temperature range of 40° C.±5° C. and continued to stir the contents for not less than 15 minutes. Then allowed the contents to settle for not less than 30 minutes. The lower layer in reactor D was separated and removed.

Charged 1970 L of water into reactor D. Waited for the contents of reactor D to cool to within the temperature range of 40° C.±5° C. and continued to stir the contents for not less than 15 minutes. Then allowed the contents to settle for not less than 30 minutes. The lower layer in reactor D was separated and removed.

Charged 1970 L of water into reactor D. Waited for the contents of reactor D to cool to within the temperature range of 40° C.±5° C. and continued to stir the contents for not less than 15 minutes. Then allowed the contents to settle for not less than 30 minutes. The lower layer in reactor D was separated and removed.

The contents of reactor D were distilled under vacuum (50–100 mm Hg) at a maximum jacket temperature of 75° C. and an internal temperature of not more than 50° C. until no more distillate came off to provide (2S,3S,5S)-2-N,N-dibenzylamino-3-hydroxy-5-(2S-(1-tetrahydro-pyrimid-2-onyl)-3-methylbutanoyl)amino-1,6-diphenylhexane.

Charged 3110 L of methanol into reactor D and stirred at 55° C.±5° C. until all of the solids were dissolved. Charged 174 kg of ammonium formate into reactor D and stirred at 55° C.±5° C. until all of the solids were dissolved.

Under a nitrogen atmosphere, charged 55 kg of palladium on carbon (50% wet 5% Pd/C) into reactor H (8,000 L, glass lined). Then twice evacuated reactor H and filled with nitrogen. Under continuing nitrogen atmosphere, transferred the contents of reactor D to reactor H. Charged 220 L of methanol to reactor D and then transferred the contents of reactor D to reactor H. The contents of reactor H were heated to 55° C.±5° C. and stirred at 55° C.±5° C. for not less than 2 hours. Then the jacket temperature of reactor H was adjusted to 45° C.±5° C.

The contents of reactor H were hot filtered through a multiplate filter (diatomaceous earth ) into reactor I. The contents of reactor I were refluxed under vacuum (50–100 mm Hg) (jacket temperature not more than 75° C. and internal temperature not more than 50° C.) until no more distillate came off.

Reactor I was then charged with 1520 L of ethyl acetate, the contents were stirred at 45° C.±5° C. until all of the solids were dissolved and the contents of reactor I were refluxed under vacuum (50–100 mm Hg) (jacket temperature not more than 75° C. and internal temperature not more than 50° C.) until no more distillate came off to provide the title compound.

The foregoing is merely illustrative of the invention and is not intended to limit the invention to the disclosed embodiments. Variations and changes that are obvious to one skilled in the art are intended to be within the scope nature of the invention which are defined in the appended claims.

What is claimed is:

1. A process for the preparation of a compound of the formula:

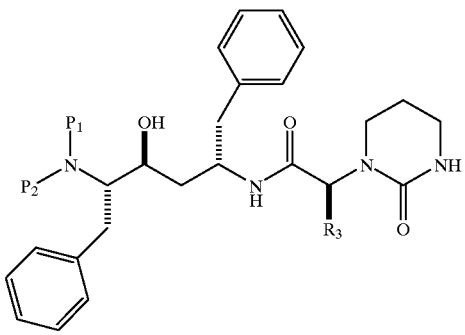

wherein $R_3$ is loweralkyl, hydroxyalkyl or cycloalkylalkyl and $P_1$ and $P_2$ are independently selected from hydrogen and an N-protecting group comprising reacting a compound of the formula:

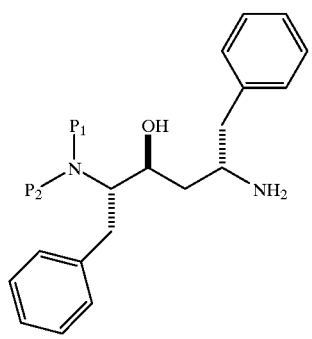

wherein $P_1$ and $P_2$ are as defined above in an inert solvent with a compound of the formula:

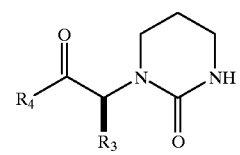

wherein $R_3$ is as defined above and $R_4$ is a nitrogen-containing heterocycle, bonded through a ring nitrogen atom to the carbonyl group, wherein the heterocycle is selected from the group consisting of imidazolyl, pyrrolyl, pyrazolyl, 1,2,3-triazolyl, 1,2,4-triazolyl, tetrazolyl, indolyl, benzimidazolyl and benzotriazolyl.

2. The process of claim 1 wherein $R_4$ is imidazolyl.

3. The process of claim 1 wherein $P_1$ and $P_2$ are each benzyl, $R_3$ is loweralkyl and $R_4$ is imidazolyl.

4. The process of claim 1 wherein $P_1$ and $P_2$ are each benzyl, $R_3$ is isopropyl and $R_4$ is imidazolyl.

5. The process according to claim 1 further comprising water.

6. The process according to claim 5 wherein the water is present in the amount of from about 1% to about 3% (weight/volume), based on the ratio of the weight of the water to the volume of the reaction mixture.

7. A process for the preparation of a compound selected from (2S,3S,5S)-2-N,N-dibenzylamino-3-hydroxy-5-(2S-(1-tetrahydro-pyrimid-2-onyl)-3-methylbutanoyl)amino-1, 6-diphenylhexane and (2S,3S,5S)-2-amino-3-hydroxy-5-(2S-(1-tetrahydro-pyrimid-2-onyl)-3-methylbutanoyl)amino-1,6-diphenylhexane comprising reacting (2S,3S,5S)-2-N,N-dibenzylamino-3-hydroxy-5-amino-1,6-diphenylhexane in an inert solvent with N-(2S-(1-tetrahydro-pyrimid-2-onyl)-3-methyl butanoyl)imidazole.

8. The process according to claim 7 further comprising water.

9. The process according to claim 8 wherein the water is present in the amount of from about 1% to about 3% (weight/volume), based on the ratio of the weight of the water to the volume of the reaction mixture.

10. A compound of the formula:

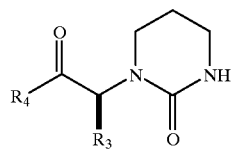

wherein $R_3$ is loweralkyl, hydroxyalkyl or cycloalkylalkyl and $R_4$ is a nitrogen-containing heterocycle, bonded through a ring nitrogen atom to the carbonyl group, selected from the group consisting of imidazolyl, pyrrolyl, pyrazolyl, 1,2,3-triazolyl, 1,2,4-triazolyl, tetrazolyl, indolyl, benzimidazolyl and benzotriazolyl.

11. A compound according to claim 10 wherein $R_3$ is loweralkyl and $R_4$ is imidazolyl.

12. A compound according to claim 10 wherein $R_3$ is isopropyl and $R_4$ is imidazolyl.

13. The compound N-(2S-(1-tetrahydro-pyrimid-2-onyl)-3-methyl butanoyl)imidazole.

* * * * *

UNITED STATES PATENT AND TRADEMARK OFFICE
CERTIFICATE OF CORRECTION

PATENT NO. : 6,372,905 B1
DATED : April 16, 2002
INVENTOR(S) : Sanjay R. Chemburkar et al.

It is certified that error appears in the above-identified patent and that said Letters Patent is hereby corrected as shown below:

<u>Column 6,</u>
Line 9, replace "only" with -- onyl --

Signed and Sealed this

Twentieth Day of August, 2002

Attest:

Attesting Officer

JAMES E. ROGAN
*Director of the United States Patent and Trademark Office*